United States Patent [19]

Campbell

[11] 4,188,390
[45] Feb. 12, 1980

[54] ANTIHYPERTENSIVE 4-AMINO-2-[4-(1,4-BENZODIOXAN-2-CARBONYL) PIPERAZIN-1-YL OR HOMOPIPERAZIN-1-YL]QUINAZOLINES

[75] Inventor: Simon F. Campbell, Deal, England

[73] Assignee: Pfizer Inc., New York, N.Y.

[21] Appl. No.: 952,317

[22] Filed: Oct. 18, 1978

[30] Foreign Application Priority Data
Nov. 5, 1977 [GB] United Kingdom ............... 46128/77
Sep. 27, 1978 [DK] Denmark ........................... 4286/78

[51] Int. Cl.² .................. A61K 31/505; C07D 405/14
[52] U.S. Cl. .................. 424/251; 260/243.3; 260/340.3; 544/291; 544/377
[58] Field of Search .............. 424/251; 260/243.3; 544/291

[56] References Cited

U.S. PATENT DOCUMENTS

| | | | |
|---|---|---|---|
| 3,511,836 | 5/1970 | Hess | 544/291 |
| 3,669,968 | 6/1972 | Hess | 544/291 |
| 4,001,237 | 1/1977 | Partyka et al. | 544/291 |

FOREIGN PATENT DOCUMENTS 2646186  4/1977  Fed. Rep. of Germany ........... 544/291

Primary Examiner—Paul M. Coughlan, Jr
Attorney, Agent, or Firm—Connolly and Hutz

[57] ABSTRACT

Compounds having the formula

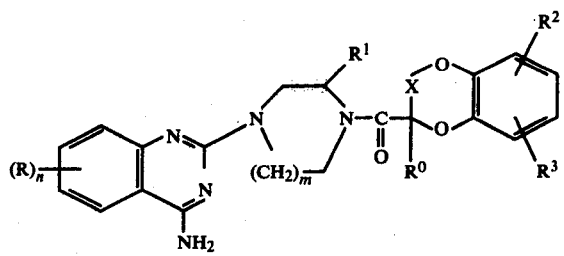

and pharmaceutically acceptable salts thereof wherein
R represents 6,7-di(lower alkoxy) or 6,7,8-tri(lower alkoxy);
m is 1 or 2,
X is —CHR¹— or —CH₂CH₂—;
each R¹ and R⁰ may be the same or different and is hydrogen or lower alkyl;
each of R² and R³ is hydrogen, lower alkoxy, lower alkyl, halogen, lower alkanoyl, lower alkoxycarbonyl, —CONR⁴R⁵ or —SO₂NR⁴R⁵ wherein each of R⁴ and R⁵ is hydrogen or lower alkyl;
processes for their preparation; and their use as regulators of the cardiovascular system, and particularly in the treatment of hypertension.

6 Claims, No Drawings

ANTIHYPERTENSIVE 4-AMINO-2-[4-(1,4-BENZODIOXAN-2-CARBONYL)PIPERAZIN-1-YL OR HOMOPIPERAZIN-1-YL]QUINAZOLINES

BACKGROUND OF THE INVENTION

1. Field of the Invention

The invention relates to therapeutic agents which are novel derivatives of 4-amino-2-(piperazin-1-yl) or homopiperazin-1-yl)quinazoline. Such compounds are useful as regulators of the cardiovascular system, and in particular, in the treatment of hypertension.

2. Description of the Prior Art

The therapeutic properties of a variety of quinazolines, including 4-amino-2-[(4-substituted)piperazin-1-yl]quinazolines are well known. U.S. Pat. No. 3,511,836 describes 4-amino-6,7-dialkoxy-2-[(4-substituted)-piperazin-1-yl]quinazolines wherein the 4-substituent is benzoyl, thenoyl or furoyl. The products are valuable hypotensive agents. Analogous 6,7,8-trialkoxy compounds, also useful as hypotensive agents, are described in U.S. Pat. No. 3,669,968.

Related antihypertensive compounds wherein the 4-substituent on the piperazinyl group is oxazolyl, thiazolyl, isoxazolyl or isothiazolyl are disclosed in U.S. Pat. No. 4,001,237.

German Specification No. 2,646,186 describes, as hypotensive agents, a series of 4-amino-6,7-dimethoxy-[2-(4-substituted)piperazin-1-yl]quinazolines wherein the 4-substituent is tetrahydro-2-furoyl or tetrahydropyran-2-carbonyl.

SUMMARY OF THE INVENTION

The novel compounds according to the invention are those having the general formula:

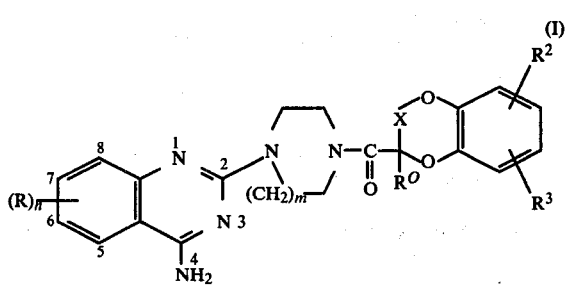

wherein (R)$_n$ represents 6,7-di(lower alkoxy) or 6,7,8-tri(lower alkoxy);

m is 1 or 2;

X represents —CHR$^1$— or —CH$_2$CH$_2$—;

each of R$^1$ and R$^0$ represents hydrogen or lower alkyl;

and R$^2$ and R$^3$, which may be the same or different, each represents hydrogen, lower alkyl, lower alkoxy, halogen, lower alkanoyl, lower alkoxycarbonyl or a group of the formula —CONR$^4$R$^5$ or —SO$_2$NR$^4$R$^5$ wherein R$^4$ and R$^5$, which may be the same or different, each represent hydrogen or lower alkyl;

and the pharmaceutically acceptable acid addition salts thereof.

In this specification, "halogen" means fluorine, chlorine, bromine or iodine. The term "lower" applied to an alkyl or alkoxy group indicates that such a straight or branched chain group contains from 1 to 6 carbon atoms, preferably from 1 to 4 carbon atoms. The term "lower" applied to an alkanoyl group means that such a straight or branched chain group contains from 2 to 6 carbon atoms, preferably from 2 to 4 carbon atoms.

Pharmaceutically acceptable acid addition salts of the compounds of the invention are those formed from acids which form non-toxic acid addition salts containing pharmaceutically acceptable anions, such as the hydrochloride, hydrobromide, sulphate or bisulphate, phosphate or acid phosphate, acetate, maleate, fumarate, succinate, lactate, tartrate, citrate, gluconate, saccharate and p-toluenesulphonate salts.

One preferred group of compounds has the formula:

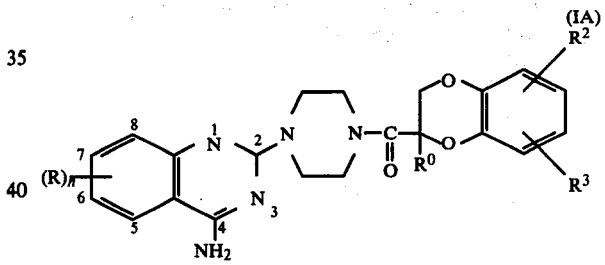

wherein (R)$_n$ represents 6,7-di(lower alkoxy) or 6,7,8-tri(lower alkoxy);

R$^0$ represents hydrogen or lower alkyl;

and R$^2$ and R$^3$, which may be the same or different, each represent hydrogen, lower alkyl, lower alkoxy, halogen, lower alkanoyl or a group of the formula —CONR$^4$R$^5$ or —SO$_2$NR$^4$R$^5$ wherein R$^4$ and R$^5$, which may be the same or different, each represent hydrogen or lower alkyl;

and the pharmaceutically acceptable acid addition salts thereof.

Another preferred group of compounds has the formula (I) wherein (R)$_n$ is 6,7-dimethoxy, 6,7-diethoxy or 6,7,8-trimethoxy; m is 1 or 2; each of R$^1$ and R$^0$ is independently H or CH$_3$; and R$^2$ and R$^3$ are each independently hydrogen, lower alkyl, lower alkoxy, halogen, lower alkanoyl, lower alkoxycarbonyl, —CONH$_2$ or SO$_2$N(CH$_3$)$_2$.

The most preferred compounds have the formula:

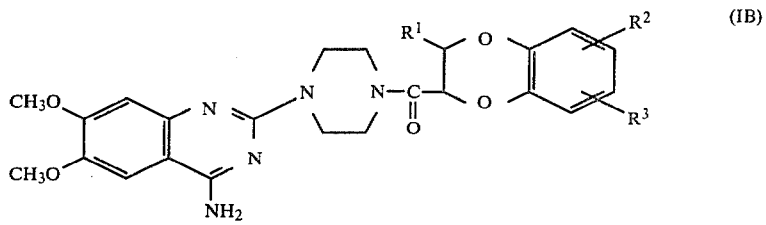

wherein $R^1$ is H or $CH_3$ and $R^2$ and $R^3$ are hydrogen, lower alkyl, lower alkoxy, halogen or lower alkanoyl.

The most preferred individual compound is 4-amino-2-[4-(1,4-benzodioxan-2-carbonyl)piperazin-1-yl]-6,7-dimethoxyquinazoline.

The compounds of the invention containing one or more asymmetric centers will exit as one or more pairs of enantiomers, and such pairs or individual isomers are separable by physical methods, e.g. by fractional crystallization of suitable salts. The invention includes the separated pairs as well as mixtures thereof, as racemic mixtures or as separated d- and l-optically-active isomeric forms.

When X represents —CHR¹— wherein $R^1$ is lower alkyl, then cis- and trans-isomerism is possible, and both isomers (and mixtures thereof) are within the scope of the invention.

DETAILED DESCRIPTION OF THE INVENTION

The compounds of the invention can be prepared in a number of ways, including the following:

(1) The compounds of the invention can be prepared by reacting an appropriately substituted quinazoline of the formula:

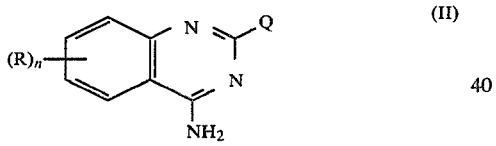

wherein Q represents a facile leaving group such as chloro, bromo, iodo, lower alkoxy or (lower alkyl)thio, with a piperazine or homopiperazine of the formula:

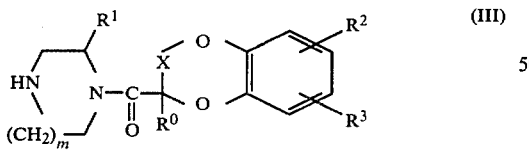

with resultant elimination of HQ. Q is preferably chloro or bromo.

The reaction is typically carried out by heating the reactants, e.g. at a temperature of from 80° to 150° C., e.g., under reflux, in an inert organic solvent, e.g. n-butanol. When the reaction is substantially complete, the product can be isolated and purified by conventional procedures. For example, in a typical procedure the reaction mixture is cooled, and the resulting crude solid product collected, washed with e.g. cold-n-butanol, and dried. The crude product can be purified in a typical procedure by dissolving it in hot aqueous dimethylformamide, filtering and concentrating the filtered solution, e.g. in vacuo. The solution is then cooled and ether added to precipitate the pure product, which can be filtered and washed with ether.

The intermediates of the formulae (II) and (III) are either known compounds or can be prepared by methods analogous to those of the prior art. For example, the intermediates of the formula (III) can be prepared according to the following reaction procedure:

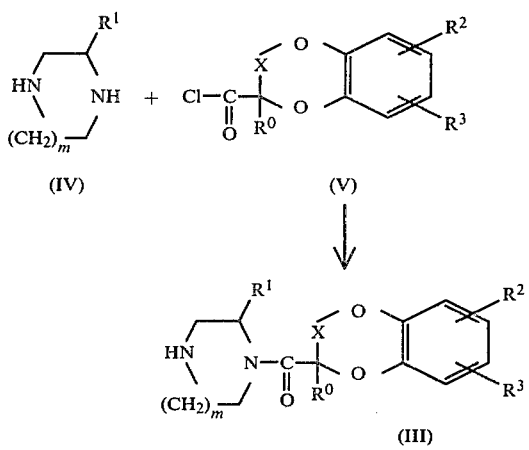

The intermediates of the formula (IV) and (V) are either known compounds or can be prepared by conventional procedures. When X is —CHR¹— wherein $R^1$ is lower alkyl, then cis- and trans- isomers of compound (V) are possible. A mixture of these isomers may be used but if a mainly cis- or trans- end product is desired then the appropriate cis- or trans- starting material can generally be prepared by an appropriate chromatographic technique on the corresponding methyl or ethyl ester, followed by conversion to the acid chloride.

(2) The compounds of the invention can also be prepared by reacting a quinazoline of the formula:

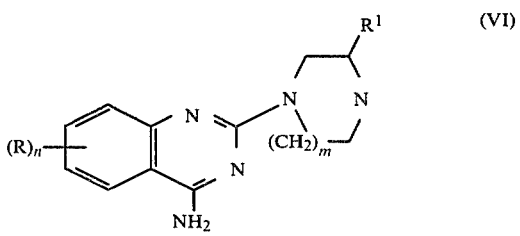

with a carboxylic acid of the formula:

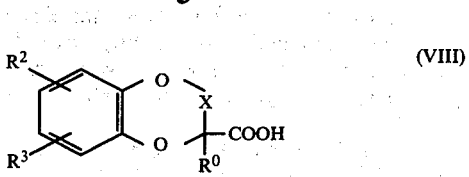

(VIII)

or with its functional equivalent as an acylating agent, e.g. an acid chloride or bromide, "activated" ester, or mixed anhydride of the compound of the formula (VII).

The acid chlorides or bromides can be prepared by conventional procedures, e.g. by reacting the free acid with, respectively, thionyl chloride or bromide.

The preferred "activated ester" is the succinimido ester of the formula:

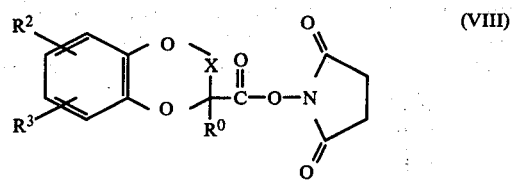

(VIII)

which again can be prepared by conventional procedures, e.g. by reacting the free acid with N-hydroxysuccinimide in the presence of a dehydrating agent, e.g. dicyclohexylcarbodiimide. Another preferred "activated ester" is the phthalimido ester.

Suitable mixed anhydrides have the formula:

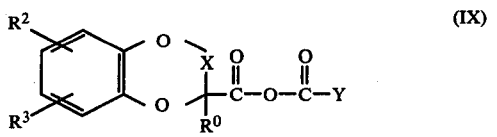

(IX)

wherein Y is a lower alkyl or lower alkoxy group, most preferably a t-butyl or iso-butoxy group. They can be prepared by conventional procedures, e.g. by reacting the free acid with the appropriate lower alkanoyl chloride or lower alkyl chloroformate, respectively, e.g. pivaloyl chloride or iso-butyl chloroformate, in the presence of a base such as triethylamine.

When the free acid form of compound (VII) is used, the reaction should generally be carried out in the presence of a dehydrating agent such as dicyclohexylcarbodiimide.

Preferably, the compounds of the formula (VII) are reacted in the form of their acid chlorides or bromides.

In a typical procedure using an acid chloride of (VII), the acid chloride in a suitable solvent, e.g. methylene chloride, is added dropwise to a stirred suspension of the quinazoline (VI) in a suitable solvent, e.g. methylene chloride. The mixture is then stirred for a few hours at room temperature, and the resulting solid then filtered off and purified by conventional technique.

When X is —CHR$^1$— wherein R$^1$ is lower alkyl, then cis-trans isomerism will be possible as mentioned in route (1).

The intermediates of the formula (VI) and (VII) can be prepared by conventional procedures.

(3) The pharmaceutically acceptable acid addition salts of the compounds of the invention can be prepared by conventional procedures, e.g. by reacting the free base with the appropriate acid in an inert organic solvent, and collecting the resulting precipitate of the salt by filtration. If necessary, the product can then be recrystallized to purify it. Often, however, the product obtained by routes (1) and (2) will be in an acid-addition salt form.

The invention also includes the pharmaceutically acceptable bioprecursors of the compounds of the formula (I) and said salts thereof.

The term "pharmaceutically acceptable bioprecursor" requires some explanation. It is of course, common practice in pharmaceutical chemistry to overcome some undesirable physical or chemical property of a drug by converting the drug into a chemical derivative which does not suffer from that undesirable property, but which, upon administration to an animal or human being, is converted back to the parent drug. For example, if the drug is not well absorbed when given to the animal or patient, by the oral route, it is possible to convert the drug into a chemical derivative which is well absorbed and which in the serum or tissues is reconverted to the parent drug. Again, if a drug is unstable in solution, it is possible to prepare a chemical derivative of the drug which is stable and can be administered in solution, but which is reconverted in the body to give the parent drug. The pharmaceutical chemist is well aware of the possibility of overcoming intrinsic deficiencies in a drug by chemical modifications which are only temporary and are reversible upon administration to the animal or patient.

For the purpose of this specification the term "pharmaceutically acceptable bioprecursor" of a compound of the formula (I) means a compound having a structural formula different from the compounds of the formula (I) but which nonetheless, upon administration to an animal or human being, is converted in the patient's body to a compound of the formula (I).

The antihypertensive activity of the compounds of the invention is shown by their ability to lower the blood pressure of conscious spontaneously hypertensive rats and conscious renally hypertensive dogs, when administered orally at doses of up to 5 mg/kg.

The compounds of the invention can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules either alone or in admixture with excipients, or in the form of elixirs or suspensions containing flavoring or coloring agents. They can be injected parenterally, for example, intramuscularly, intravenously or subcutaneously. For parenteral administration, they are best used in the form of a sterile aqueous solution which can contain other solutes, for example, enough salt or glucose to make the solution isotonic.

Thus the invention also provides a pharmaceutical composition comprising a compound of the formula (I) or pharmaceutically acceptable acid addition salt thereof together with a pharmaceutically acceptable diluent or carrier.

The compounds of the invention can be administered to humans for the treatment of hypertension by either the oral or parenteral routes, and may be administered orally at dosage levels approximately within the range 1 to 20 mg./day for an average adult patient (70 kg.), given in a single dose or up to 3 divided doses. Intravenous dosage levels would be expected to be about one-fifth to one-tenth of the daily oral dose. Thus for an average adult patient, individual oral doses in tablet or capsule form will be approximately in the range from 1 to 50 mg. of the active compound. Variations will necessarily occur depending on the weight and condition of the subject being treated and the particular route of administration chosen as will be known to those skilled in the art.

The invention yet further provides a method of treating an animal, including a human being, having hypertension, which comprises administering to the animal an antihypertensive amount of a compound of the formula (I) or pharmaceutically acceptable acid addition salt thereof or pharmaceutical composition as defined above.

The following Examples illustrate the invention:

EXAMPLE 1

4-Amino-2-[4-(1,4-benzodioxan-2-carbonyl)piperazin-1-yl]-6,7-dimethoxyquinazoline

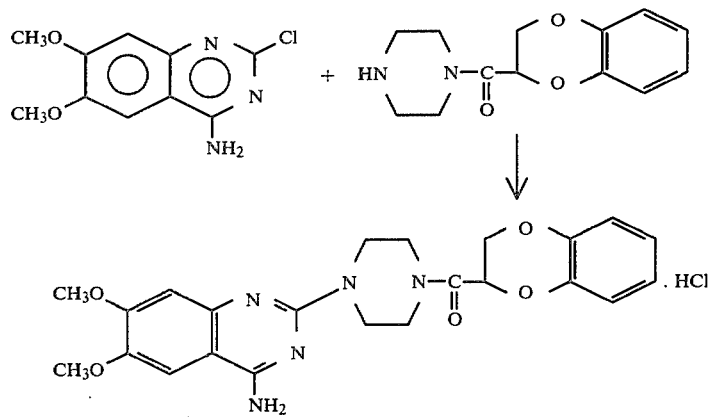

4-Amino-2-chloro-6,7-dimethoxyquinazoline (140 g.) and N-(1,4-benzodioxan-2-carbonyl)piperazine (150 g.) were stirred together under reflux in n-butanol (2 l.) for 3½ hours. The mixture was then cooled to 80° C., the solid product collected, washed with cold n-butanol (2×250 ml.), and dried. The crude product was dissolved in hot (80° C.) dimethylformamide (530 ml.) and water (130 ml.), filtered, concentrated in vacuo to about 300 ml., then cooled and ether (1.8 l.) added. The solid so obtained was collected and washed with ether to give 4-amino-2-[4-(1,4-benzodioxan-2-carbonyl)piperazin-1-yl]-6,7-dimethoxyquinazoline hydrochloride (215 g.), m.p. 289°–290° C.

Analysis %: Found: C, 56.9; H, 5.4; N, 14.4. Calculated for $C_{23}H_{25}N_5O_5 \cdot HCl$: C, 56.6; H, 5.4; N, 14.4.

EXAMPLE 2

4-Amino-2-[4-(1,4-benzodioxan-2-carbonyl)piperazin-1-yl]-6,7,8-trimethoxyquinazoline 4-amino-2-chloro-6,7,8-trimethoxyquinazoline (1 g.) and N-(1,4-benzodioxan-2-carbonyl)piperazine (1.168 g.) were heated under reflux in n-butanol (67 ml.) with triethylamine (1.87 g.) for 24 hours. Further N-(1,4-benzodioxan-2-carbonyl)piperazine (0.026 g.) was then added and the mixture heated under reflux for an additional 30 hours. Butanol was then removed in vacuo and the residue partitioned between aqueous sodium carbonate solution and chloroform. The combined chloroform extracts were washed with water, dried (Na₂SO₄) and evaporated in vacuo to leave a solid (3.4 g.) which was taken up in the minimum quantity of dimethylformamide then set aside at 0° C. overnight. Ether was then added and the cloudy solution further cooled to yield 4-amino-2-[4-(1,4-benzodioxan-2-carbonyl)piperazin-1-yl]-6,7,8-trimethoxyquinazoline (0.58 g.), m.p. 269°–271° C.

Analysis %: Found: C, 59.3; H, 5.6; N, 14.1. Calculated for $C_{24}H_{27}N_5O_6$: C, 59.9; H, 5.7; N, 14.6.

EXAMPLE 3

4-Amino-2-[4-(1,4-benzodioxan-2-carbonyl)piperazin-1-yl]-6,7-diethoxyquinazoline 4-Amino-2-chloro-6,7-diethoxyquinazoline (0.33 g.) and N-(1,4-benzodioxan-2-carbonyl)piperazine (0.32 g.) were heated under reflux in n-butanol (30 ml.) overnight. The mixture was then evaporated in vacuo and the residue partitioned between sodium carbonate solution and chloroform. The combined chloroform extracts were washed with water, dried (Na₂SO₄), evaporated in vacuo and the residue chromatographed on silica gel (70 g.) using chloroform/methanol (0–5%) as eluent. Similar fractions were combined, evaporated in vacuo then redissolved in chloroform/methanol and treated with ethereal hydrogen chloride. The solution was then evaporated in vacuo and the residue recrystallized from isopropanol to give 4-amino-2-[4-(1,4-benzodioxan-2-carbonyl)piperazin-1-yl]-6,7-diethoxyquinazoline hydrochloride.2 1/2 hydrate (0.19 g.), m.p. 180°–184° C. (decomp.)

Analysis %: Found: C, 53.3; H, 5.6; N, 12.2. Calculated for $C_{25}H_{29}N_5O_5 \cdot HCl.2$ 1.2 H₂O: C, 53.5; H, 6.3; N, 12.5.

EXAMPLE 4

4-Amino-2-[4-(1,4-benzodioxan-2-carbonyl)homopiperazin-1-yl]-6,7-dimethoxyquinazoline 4-Amino-2-chloro-6,7-dimethoxyquinazoline (1.58 g.) and N-(1,4-benzodioxan-2-carbonyl)homopiperazine (2.0 g.) were heated under reflux in n-butanol (114 ml.) for 60 hours. The mixture was then cooled, butanol removed in vacuo and the solid residue triturated with ether, taken up in hot methanol, filtered and cooled. The solid product was collected, then the residual solution was evaporated in vacuo and the residue taken up in hot isopropanol, cooled, filtered, then re-evaporated in vacuo. The residue was combined with the original solid product, treated with cold methanol, and recrystallized from ethanol to give 4-amino-2-[4-(1,4-benzodioxan-2-carbonyl)homopiperazin-1-yl]-6,7-dimethoxyquinazoline hydrochloride (0.57 g.), m.p. 250°–251° C.

Analysis %; Found: C, 57.2; H, 5.4; N, 13.8. Calculated for $C_{24}H_{27}N_5O_5 \cdot HCl$: C, 57.4; H, 5.6; N, 14.0.

EXAMPLE 5

4-Amino-2-[4-(6-methoxy-1,4-benzodioxan-2-carbonyl)piperazin-1-yl]-6,7-dimethoxyquinazoline

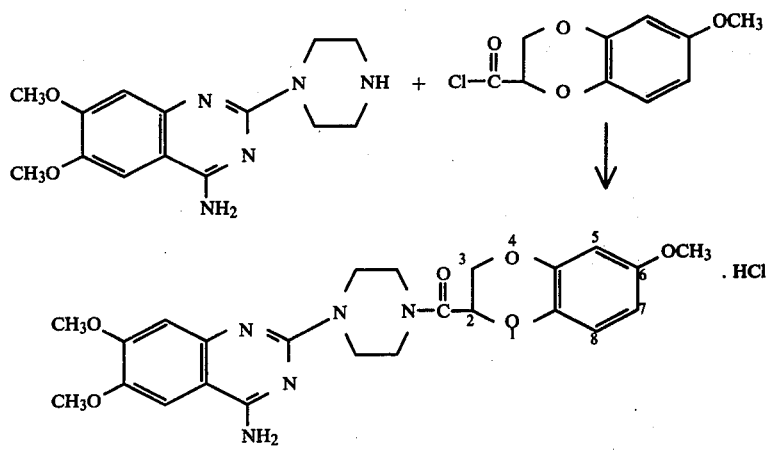

A solution of 6-methoxy-1,4-benzodioxan-2-carbonyl chloride (2.17 g.) (prepared from the acid and thionyl chloride) in dichloromethane (25 ml.) was added dropwise to a stirred suspension of 4-amino-2-piperazin-1-yl-6,7-dimethoxy-quinazoline (2.48 g.) in methylene chloride (50 ml.) at room temperature. After the addition was complete, the mixture was stirred at room temperature for 4 hours, then filtered and the solid suspended in aqueous potassium carbonate solution and extracted with chloroform. The combined extracts were washed with water, dried ($Na_2SO_4$) and evaporated in vacuo to leave a solid residue (4.15 g.) which was chromatographed on silica (160 g.) and eluted with chloroform then chloroform-methanol (2.5%). Similar fractions (t.l.c.) were combined, evaporated in vacuo then the residue taken up in ethyl acetate-methanol and treated with ethereal hydrogen chloride. Addition of further ether followed by cooling yielded a solid which was collected and recrystallized from methanol to give 4-amino-2-[4-(6-methoxy-1,4-benzodioxan-2-carbonyl)-piperazin-1-yl-]-6,7-dimethoxyquinazoline hydrochloride hydrate (0.95 g.), m.p. 220°–222° C.

Analysis %: Found: C, 53.3; H, 5.5; N, 13.4. Calculated for $C_{24}H_{27}N_5O_6 \cdot HCl \cdot H_2O$: C, 53.8; H, 5.6; N, 13.1.

EXAMPLES 6–24

The following compounds were prepared similarly to Example 5, starting from 4-amino-2-piperazin-1-yl (or 2-[3-methylpiperazin-1-yl])-6,7-dimethoxy-quinazoline and the appropriate carbonyl chloride.

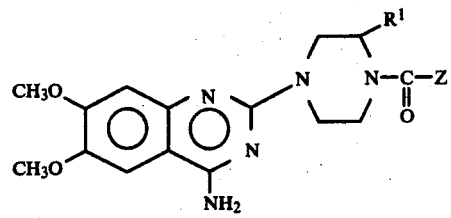

| Example No. | Z | $R^1$ | Form Isolated and m.p. (°C.) | Analysis % (Theoretical in Brackets) C | H | N |
|---|---|---|---|---|---|---|
| 6 | ![structure with CH3 at position 7, mixture of 8- and 5-isomers] | H | Hydrochloride, hemihydrate 238°–240° | 56.2 (56.4 | 5.4 5.7 | 13.9 13.7) |
| 7 | ![structure with CH(CH3)2 at position 7, mixture of 8- and 5-isomers] | H | Hydrochloride, hemihydrate 225°–230° | 58.0 (57.9 | 6.2 6.2 | 13.3 13.0) |

-continued

| Example No. | Z | R¹ | Form Isolated and m.p. (°C.) | Analysis % (Theoretical in Brackets) | | |
|---|---|---|---|---|---|---|
| | | | | C | H | N |
| 8 | 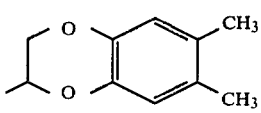 | H | Hydrochloride, hemihydrate 286°–288° | 57.5 (57.2 | 5.8 6.0 | 13.3 13.3) |
| 9 | 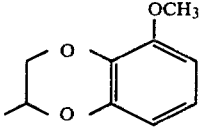 | H | Hydrochloride, hemihydrate 268°–270° | 54.1 (54.7 | 5.5 5.5 | 13.9 13.3) |
| 10 | 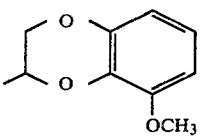 | H | Hydrochloride, hydrate, 230° (dec.) | 53.4 (53.8 | 5.3 5.6 | 12.8 13.1) |
| 11 | 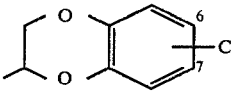 mixtures of 6- and 7-isomers) | H | Hydrochloride, hydrate, 280°–281° | 52.3 (52.0 | 4.8 4.9 | 12.8 13.2) |
| 12 | 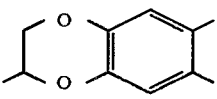 | H | Hemihydrate 242°–243° | 52.5 (52.2 | 4.3 4.6 | 13.2 13.2) |
| 13 | 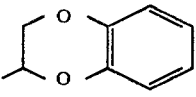 (−) | H | Hydrochloride, 297°–280°, $\alpha_D = -99.3°$ (0.4% in DMF) | 56.5 (56.5 | 5.6 5.4 | 14.1 14.4) |
| 14 | 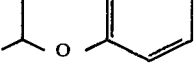 (+) | H | Hydrochloride 284°–286°, $\alpha_D = +95°$ (0.4% in DMF) | 56.2 (56.6 | 5.4 5.4 | 14.5 14.4) |
| 15 | 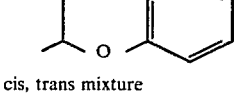 cis, trans mixture | H | Hydrochloride hydrate, 237°–240° | 55.0 (55.4 | 5.5 5.8 | 13.6 13.5) |
| 16 | 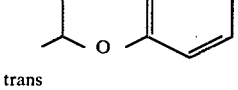 trans | H | Hydrochloride hydrate, 242°–243° | 55.8 (55.4 | 5.7 5.8 | 13.1 13.5) |
| 17 | 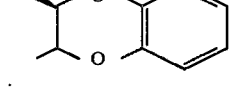 cis | H | Hydrochloride dihydrate, 214°–215° | 54.0 (53.6 | 5.5 6.0 | 12.7 13.0) |
| 18 | 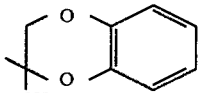 | H | Hydrochloride hydrate, 234°–237° | 55.6 (55.4 | 5.4 5.8 | 13.3 13.5) |
| 19 | 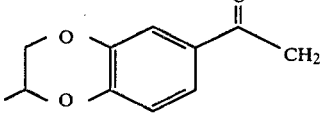 | H | Hydrochloride hemihydrate, 272° | 55.6 (55.7 | 5.2 5.4 | 13.0 13.0) |

-continued

| Example No. | Z | R¹ | Form Isolated and m.p. (°C.) | Analysis % (Theoretical in Brackets) C | H | N |
|---|---|---|---|---|---|---|
| 20 | (structure: 1,4-benzodioxan with COCH₃ substituent) | H | Hydrochloride hydrate, 230° | 54.4 (54.8 | 5.2 5.5 | 12.8 12.8) |
| 21 | (structure: 1,4-benzodioxan with SO₂N(CH₃)₂ at 6/7 position) (mixture of 6- and 7-isomers) | H | Hydrochloride hydrate, 232°–234° (dec.) | 48.6 (49.0 | 5.3 5.4 | 13.5 13.7) |
| 22 | (structure: benzo-fused 7-membered dioxepine) | H | Hydrochloride sesqui-methanolate 205°–207° | 55.3 (55.7 | 6.1 6.2 | 12.9 12.7) |
| 23 | (structure: 1,4-benzodioxan) | CH₃ | Oxalate sesqui-hydrate, 176°–179° | 53.8 (53.6 | 5.4 5.5 | 11.6 12.0) |
| 24 | (structure: 1,4-benzodioxan with COOC₂H₅ at 6/7) (mixture of 6- and 7-isomers) | H | Hydrochloride di-hydrate, 208°–210° (hygroscopic) | 52.2 (52.4 | 5.2 5.8 | 11.4 11.8) |

EXAMPLE 25

4-Amino-6,7-dimethoxy-2-[4-(a mixture of 6- and 7-carbamoyl-1,4-benzodioxan-2-carbonyl)piperazino]-quinazoline hydrochloride Dicyclohexylcarbodiimide (2.06 g.) and N-hydroxysuccinimide (1.15 g.) were added to a stirred solution of a mixture of 6- and 7-carbamoyl-1,4-benzodioxan-2-carboxylic acid (2.23 g.) in dimethylformamide (70 ml.) at 0° C. The mixture was stirred at 0° C. for 1 hour. 4-Amino-6,7-dimethoxy-2-piperazino-quinazoline (2.8 g.) was then added and the resultant mixture was stirred at room temperature overnight. The reaction was then filtered, the filtrate diluted with ether (500 ml.) and the resulting oily precipitate collected. The product was partitioned between chloroform/isopropanol/sodium bicarbonate solution, the chloroform layer separated, washed with water and evaporated in vacuo. The residue was chromatographed on silica and elution with chloroform-methanol (3%) gave a crude product which on treatment with ethereal hydrogen chloride solution and recrystallization from methanol/water/ether/dimethylformamide followed by methanol/waterdimethylformamide yielded 4-amino-6,7-dimethoxy-2-[4-(6- and 7-(mixture)-carbamoyl-1,4-benzodioxan-2-carbonyl)piperazino]-quinazoline hydrochloride hydrate, m.p. 228°–235° C. (dec.).

Further recrystallization provided an analytical sample, m.p. 245°–248° C.

Analysis %: Found: C, 52.6; H, 5.5; N, 14.6. Calculated for $C_{24}H_{26}N_6O_6 \cdot HCl \cdot H_2O$: C, 52.5; H, 5.3; N, 15.3.

High pressure liquid chromatographic analysis indicated that the product was a mixture of 6- and 7-isomers in the ratio of 7:3.

EXAMPLE 26

The procedure of Example 4 is repeated but using the appropriate 4-amino-2-chloro-(R)ₙ-quinazoline N-(1,4-benzodioxan-2-carbonyl)piperazine or homopiperazine to produce the following compounds:

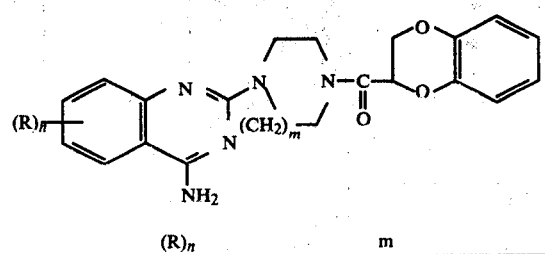

| (R)ₙ | m |
|---|---|
| 6,7-di-n-propoxy | 1 and 2 |
| 6,7-di-isopropoxy | 1 and 2 |
| 6,7-di-n-butoxy | 1 and 2 |
| 6,7-8-triethoxy | 1 and 2 |
| 6,7,8-tri-n-propoxy | 1 and 2 |
| 6,7,8-tri-n-butoxy | 1 and 2 |

EXAMPLE 27

Following the procedure of Example 5 but using the appropriate 4-amino-2-piperazin-1-yl (or homopiperazin-1-yl)-(R)ₙ-quinazoline and the appropriate 1,4-benzodioxan-2-carbonyl chloride reactant, the compounds tabulated below are prepared:

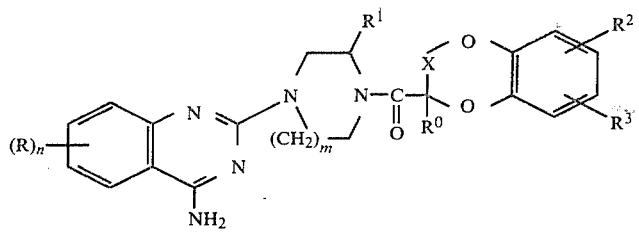

| (R)$_n$ | m | R$^1$ | R$^0$ | X | R$^2$ | R$^3$ |
|---|---|---|---|---|---|---|
| 6,7-diethoxy | 1 | H | H | CH$_2$ | H | H |
| 6,7-diethoxy | 2 | H | H | CH$_2$ | H | H |
| 6,7-diethoxy | 1 | H | H | CH$_2$CH$_2$ | H | H |
| 6,7-di-n-butoxy | 2 | H | H | CH$_2$CH$_2$ | H | H |
| 6,7-di-n-propoxy | 2 | H | H | CH(CH$_3$) | 6-Cl | 7-Cl |
| 6,7-di-n-butoxy | 1 | H | H | CH$_2$CH$_2$ | 6-OCH$_3$ | H |
| 6,7-di-isopropoxy | 2 | CH$_3$ | H | CH$_2$CH$_2$ | 6-CH$_3$ | 7-CH$_3$ |
| 6,7-dimethoxy | 1 | CH$_3$ | CH$_3$ | CH$_2$ | H | H |
| 6,7-dimethoxy | 2 | CH$_3$ | CH$_3$ | CH$_2$ | H | H |
| 6,7,8-trimethoxy | 2 | H | H | CH$_2$ | H | H |
| 6,7,8-trimethoxy | 2 | H | H | CH$_2$CH$_3$ | H | H |
| 6,7,8-triethoxy | 1 | H | H | CH$_2$ | 6-COCH$_3$ | H |
| 6,7,8-tri-n-propoxy | 1 | CH$_3$ | H | CH$_2$ | 8-OCH$_3$ | H |
| 6,7,8-tri-n-butoxy | 2 | H | H | CH$_2$ | 6-Cl and 7-Cl | H |
| 6,7-dimethoxy | 2 | H | CH$_3$ | CH$_2$ | 6-CONH$_2$ and 7-CONH$_2$ | H |
| 6,7-diethoxy | 1 | H | CH$_3$ | CH$_2$CH$_2$ | 7-COCH$_3$ | H |

The following illustrates the preparation of certain starting materials.

PREPARATION 1

(A) N-(1,4-Benzodioxan-2-carbonyl)piperazine

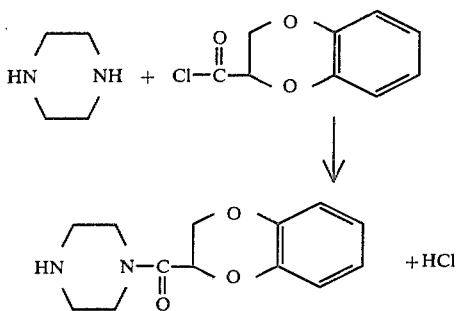

A suspension of piperazine (11.88 g.) and sodium acetate (20.30 g.) in a mixture of water (70 ml.) and acetone (95 ml.) was stirred at 10°–15° C., then concentrated hydrochloric acid was added (about 35 ml.) until the pH of the solution reached 1.5. 1,4-Benzodioxan-2-carbonyl chloride (31.0 g.) and sodium hydroxide (5N, about 45 ml.) were then added portionwise while maintaining the temperature at 10°–15° C., the sodium hydroxide maintaining the pH at 1.7–2.2. After the addition was complete, the pH was adjusted to 2.0 by the addition of sodium hydroxide, the suspension was stirred for a further 30 minutes. Water was then added until a homogenous solution resulted, the acetone removed in vacuo, and the aqueous phase was basified to pH 8–9 with sodium hydroxide (5N), re-extracted with chloroform (3×200 ml.) and the extracts washed with water, dried (MgSO$_4$) and evaporated in vacuo. The oily residue was dissolved in ethyl acetate, treated with ethereal hydrogen chloride, evaporated in vacuo and the solid residue triturated with ether, followed by recrystallization from methanol to give N-(1,4-benzodioxan-2-carbonyl)-piperazine hydrochloride (4.85 g.), m.p. 265°–267° C.

Analysis %: Found: C, 54.6; H, 5.5; N, 9.7. Calculated for C$_{13}$H$_{16}$N$_2$O$_3$.HCl: C, 54.8; H, 6.0; N, 9.8.

PREPARATION 2

6-Methoxy-1,4-benzodioxan-2-carboxylic Acid

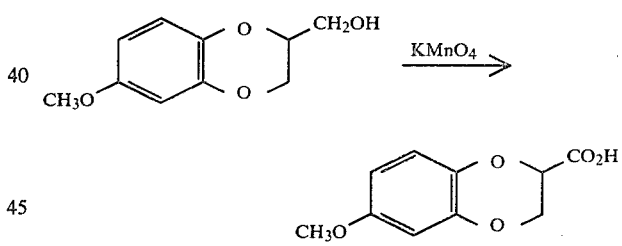

Finely ground potassium permangante (5.02 g.) was added in four portions to a stirred suspension of 2-hydroxymethyl-6-methoxy-1,4-benzodioxan (4.52 g.) in potassium hydroxide solution (1.47 g., in 42 ml. water) at 5° C. During the reaction, the temperature was maintained at 5°–15° C. then after addition was complete, stirring was continued at room temperature for 4 hours then the reaction set aside overnight.

Manganese dioxide was removed by filtration, the solid washed with water and the combined aqueous phase acidifed (pH 1) with concentrated hydrochloric acid, cooled, then extracted with chloroform.

The combined chloroform extracts were washed with sodium hydroxide solution (5N, 2×40ml.) then the basic phase further washed with chloroform, cooled, acidified (pH 1) with concentrated hydrochloric acid and re-extracted with chloroform. This latter chloroform solution was washed with water, dried (Na$_2$SO$_4$) and evaporated to leave a crude residue of 6-methoxy-1,4-benzodioxan-2-carboxylic acid (2.33 g.). A sample was recrystallized from water, m.p. 120°–121° C.

Analysis %: Found: C, 57.1; H, 4.8. Calculated for $C_{10}H_{10}O_5$: C, 57.1; H, 4.8.

PREPARATION 3

8- and 5-(mixture)-Isopropyl-1,4-benzodioxan-2-carboxylic Acid (A) A stirred solution of 3-isopropyl catechol (23 g.) in acetone (250 ml.) was heated under reflux then potassium carbonate (28 g.) added. The heterogenous mixture was refluxed for a further 15 minutes followed by the dropwise addition of methyl 2,3-dibromopropionate (10 g.). Three further batches of potassium carbonate (28 g.) and methyl 2,3-dibromopropionate (10 g.) were added in a similar fashion then the mixture stirred under reflux for 12 hours. The mixture was then evaporated, the residue diluted with water (700 ml.), extracted with chloroform and the combined extracts washed with water, dried ($MgSO_4$) and evaporated. The residual oil was distilled to give methyl 8(5)-isopropyl-1,4-benzodioxan-2-carboxylate (29.3 g.), b.p. 115°–120° C./0.5 mm. $C^{13}$ NMR spectroscopy confirmed the product was a mixture of 8- (71%) and 5-(29%) isomers.

(B) The above product (29.0 g.) in sodium hydroxide solution (160 ml., 2.5N) was heated at 100° C. for one-half hour then the resulting solution was cooled and acidified with concentrated hydrochloric acid. The mixture was extracted with chloroform (3×200 ml.), the combined extracts dried ($MgSO_4$) and evaporated in vacuo to leave an oil (18 g.) which solidified on standing. Recrystallization from methanol gave a mixture of 8-and 5-isopropyl-1,4-benzodioxan-2-carboxylic acid, m.p. 86°–88° C.

Analysis %: Found: C, 64.7; H, 6.3. Calculated for $C_{12}H_{14}O_4$: C, 64.9; H, 6.3.

High pressure liquid chromatography indicated that the product was a mixture of the 8- (86%) and 5- (13%) isomers. [Spectra Physics 3,500 cs Machine; column, 1'×¼" O.D. μ Bondapak (Trademark of Waters Associates) C-18; eluant, acetonitrile (1)/0.15M potassium hydrogen phosphate buffer pH 3.5 (2) ; flow rate, 14 ml./min.; pressure 600 p.s.i.].

PREPARATION 4

A mixture of 8- and 5-Methyl-1,4-benzodioxan-2-carboxylic Acid

Potassium permanganate (23.15 g.) was added in three portions to a stirred suspension of a mixture of 8- and 5-methyl-2-hydroxymethyl-1,4-benzodioxan (20 g.) in potassium hydroxide solution (6.5 g. in 187 ml. $H_2O$) at 5° C. The reaction temperature was maintained below 15° C. and after the addition was complete, the reaction was stirred at room temperature for 4 hours. Manganese dioxide was removed by filtration, the filtrate cooled, acidified with concentrated hydrochloric acid and the oily product which separated on further cooling was extracted with chloroform. The chloroform extracts were washed with 5N sodium hydroxide solution, the basic layer washed with chloroform then acidified with concentrated hydrochloric acid to pH 1. The acidic solution was extracted with chloroform, the combined extracts washed with brine, dried ($MgSO_4$) and evaporated in vacuo to leave a mixture of 8- and 5-methyl-1,4-benzodioxan-2-carboxylic acid (7.3 g.) as a treacle-like residue with consistent spectroscopic properties. A small sample was esterified with diazomethane and was shown by gas chromatography to be a mixture of isomers (5:2).

PREPARATION 5

6,7-Dimethyl-1,4-benzodioxan-2-carboxylic Acid

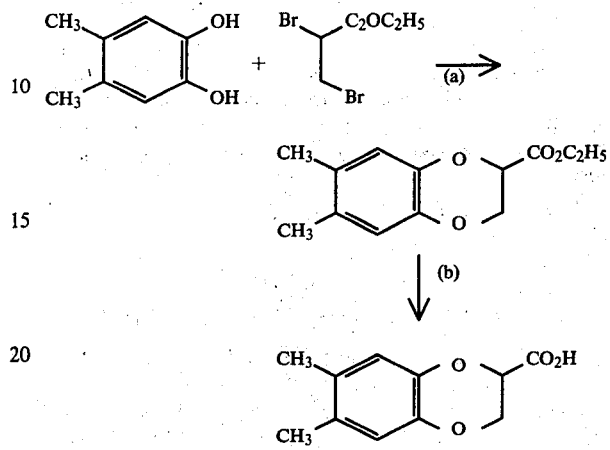

(A) A stirred solution of 4,5-dimethylcatechol (7.0 g.) in dry acetone (45 ml.) was heated under reflux, then potassium carbonate (5 g.) was added followed by the dropwise addition of ethyl dibromopropionate (3.5 g.). The addition procedure was repeated a further three times over 1¼ hours then the reaction was stirred under reflux for a further 3¾ hours. After cooling, the mixture was filtered, the solids washed well with acetone then the combined filtrate concentrated in vacuo. Water (35 ml.) was added, the resulting solid collected, washed with petrol then taken up in ether. The ethereal solution was washed with water, dried ($Na_2SO_4$) and evaporated in vacuo to give ethyl 6,7-dimethyl-1,4-benzodioxan-2-carboxylate (10.17 g.), m.p. 70°–71° C.

Analysis %: Found: C, 65.7; H, 6.8. Calculated for $C_{13}H_{16}O_4$: C, 66.1; H, 6.8.

(B) Hydrolysis of the above ester (5.0 g.) with sodium hydroxide (10%, 13 ml.) in ethanol (125 ml.) as described for related compounds (J. A. C. S., 77, 5374 [1956]) gave crude 6,7-dimethyl-1,4-benzodioxan-2-carboxylic acid (4.04 g.). A sample was recrystallized from water, m.p. 150°–151° C.

Analysis %: Found: C, 63.9; H, 6.0. Calculated for $C_{11}H_{12}O_4$: C, 63.5; H, 5.8.

PREPARATION 6

6,7-Dichloro-1,4-benzodioxan-2-carboxylic Acid

Hydrolysis of ethyl 6,7-dichloro-1,4-benzodioxan-2-carboxylate (5.0 g.) with sodium hydroxide (10%, 10.9 ml.) in ethanol (50 ml.) gave 6,7-dichloro-1,4-benzodioxan-2-carboxylic acid (3.4 g.) m.p. 155°–158° C. with a consistent NMR spectrum and identical Rf (TLC) with an authentic sample.

PREPARATION 7

8-Methoxy-1,4-benzodioxan-2-carboxylic Acid

8-Methoxy-1,4-benzodioxan-2-carboxamide (2.41 g.) in 50% hydrochloric acid (35 ml.) was stirred at 100° C. for 1 hour. The resulting solution was cooled, diluted with water (200 ml.), extracted with chloroform (3×100 ml.) then the extracts dried ($MgSO_4$) and evaporated in vacuo. The solid residue (1.8 g.) was recrystallized from water (m.p. 75°–78° C.) then from ethyl acetate/hexane to give 8-methoxy-1,4-benzodioxan-2-carboxylic acid, m.p. 131°–132° C.

Analysis %: Found: C, 56.9; H, 4.8. Calculated for $C_{10}H_{10}O_5$: C, 57.1; H, 4.8.

PREPARATION 8

5-Methoxy-1,4-benzodioxan-2-carboxylic Acid

This compound was prepared by the method of Preparation 7 starting with 5-methoxy-1,4-benzodioxan-2-carboxamide. The product was crystallized from water, m.p. 85°–87° C., then from ethyl acetate/hexane to give 5-methoxy-1,4-benzodioxan-2-carboxylic acid, m.p. 139°–141° C.

Analysis %: Found: C, 56.9; H, 4.8. Calculated for $C_{10}H_{10}O_5$: C, 57.1; H, 4.8.

PREPARATION 9

6-Acetyl-1,4-benzodioxan-2-carboxylic Acid

Jones' reagent (11.6 ml.) was added dropwise to a stirred solution of 6-acetyl-2-hydroxymethyl-1,4-benzodioxan (4.0 g.) in acetone (70 ml.) at 10°–15° C. The reaction was stirred at room temperature for 18 hours then diluted with isopropanol/water/chloroform, the organic layer separated and evaporated in vacuo. The residue was redissolved in chloroform, extracted with saturated sodium carbonate solution (2×30 ml.) then the basic phase washed with chloroform, cooled and acidified to pH 1 with concentrated hydrochloric acid. The acidic solution was extracted with chloroform, the combined extracts washed with saturated brine, dried ($Na_2SO_4$) and evaporated in vacuo to give 6-acetyl-1,4-benzodioxan-2-carboxylic acid (1.56 g.), m.p. 159°–162° C. A sample was recrystallized from ethanol/ethyl acetate, m.p. 174°–175° C.

Analysis %: Found: C, 59.0; H, 4.8. Calculated for $C_{11}H_{10}O_5$: C, 59.5; H, 4.5.

PREPARATION 10

7-Acetyl-1,4-benzodioxan-2-carboxylic Acid (A) A solution of methyl 2,3-dibromopropionate (13 ml.) in acetone (50 ml.) was added dropwise over ½ hour, to a stirred suspension of 3,4-dihydroxyacetophenone (15.1 g.) and anhydrous potassium carbonate (28 g.) in acetone (100 ml.) heated under reflux. The mixture was stirred under reflux for 4 hours, then evaporated in vacuo and the residue partitioned between chloroform/water. The chloroform extracts were washed with water, dried ($MgSO_4$) and evaporated to leave a mixture (18 g.) of 6- and 7-acetyl-1,4-benzodioxan-2-carboxylic acid methyl ester in the ratio of 2:1 as determined by $C^{13}$ NMR spectroscopy. A sample of this crude product was recrystallized from isopropanol, m.p. 68°–80° C.

Analysis %: Found: C, 60.7; H, 4.9. Calculated for $C_{12}H_{12}O_5$: C, 61.0; H, 5.1.

(B) Aqueous sodium hydroxide solution (1.2 g., in 5 ml. water) was added to a stirred solution of the product (7 g.) from (A) in ethanol (25 ml.) at 15° C. The reaction temperature was maintained below 25° C. for ½ hour then the mixture evaporated in vacuo, the residue triturated with water, acidified with concentrated hydrochloric acid and extracted with chloroform. The combined chloroform extracts were dried ($MgSO_4$), evaporated in vacuo and the residue (1.46 g.) recrystallized from ethyl acetate/methanol to give 7-acetyl-1,4-benzodioxan-2-carboxylic acid, m.p. 167°–168° C.

Analysis %: Found: C, 59.0; H, 4.5. Calculated for $C_{11}H_{10}O_5$: C, 59.5; H, 4.5.

High pressure liquid chromatography (HPLC) indicated isomeric purity of ~96% [Spectra Physics, 3,500 CS Machine; column 1'×¼" O.D. μ-Bondapak (Trademark of Waters Associates) C-18; eluant, acetonitrile (1)/0.05 M potassium hydrogen phosphate buffer pH 4.5 (2); flow rate 0.6 ml./min.; pressure 780 p.s.i.].

The acidic aqueous phase was evaporated in vacuo, the residue extracted with methanol, the combined extracts evaporated in vacuo and the product (5.5 g.) recrystallized from ethyl acetate/methanol to give 6-acetyl-1,4-benzodioxan-2-carboxylic acid. HPLC showed only one component which corresponded to an authentic sample prepared by Preparation 9.

PREPARATION 11

(A) (+) 1,4-Benzodioxan-2-carboxylic Acid 1,4-Benzodioxan-2-carboxylic acid (21.6 g.) and (+) dehydroabietylamine (34.26 g.) were mixed together in hot industrial methylated spirits (1000 ml.) then allowed to stand at room temperature for 24 hours. The precipitate which formed was collected (20 g.), the filtrate concentrated to 600 ml. and left for 48 hours when further solid product (4 g.) formed. The combined product (24 g., m.p. 204°–210° C.) was repeatedly crystallized from industrial methylated spirits/methanol to constant m.p. 229°–230° C. (3.0 g.) then the mother liquors from the last two recrystallizations were combined, reduced in volume and the solid product (5.6 g.) collected. This salt was converted to the free carboxylic acid (5.5 g.), $\alpha_D$+60.1° (1% in chloroform) in the standard manner then recrystallized twice from toluene to give (+)1,4-benzodioxan-2-carboxylic acid (0.23 g.), m.p. 98°–99° C., $\alpha_D = +62.1°$ (1% solution in chloroform).

Analysis %: Found: C, 60.3; H, 4.4. Calculated for $C_9H_8O_4$: C, 60.0; H, 4.5.

(B) (−) 1,4-Benzodioxan-2-carboxylic Acid

The initial mother liquors (600 ml.) from the previous experiment were evaporated in vacuo and the oily residue was taken up in acetone (250 ml.) then set aside until crystallization was complete. The solid product (10.0 g.) was collected, crystallized from acetone then the salt (6.0 g.) converted to the free acid in the standard manner using dilute sulfuric acid. The crude product was taken up in chloroform, chromatographed on silica gel (10×50 mm. column size) eluted with chloroform, evaporated in vacuo then crystallized from toluene to give (−) 1,4-benzodioxan-2-carboxylic acid (0.90 g.), m.p. 98°–99° C., $\alpha_D = -66.1°$ (1% solution in chloroform).

Analysis %: Found: C, 59.9; H, 4.5. Calculated for $C_9H_8O_4$: C, 60.0; H, 4.5.

PREPARATION 12

N-(1,4-Benzodioxan-2-carbonyl)homopiperazine

This compound was prepared as in Preparation 1 using homopiperazine in place of piperazine. A sample of the hydrochloride salt was recrystallized from methanol, m.p. 189° C.

Analysis %: Found: C, 56.2; H, 6.2.; N, 9.3. Calculated for $C_{14}H_{18}N_2O_3 \cdot HCl$: C, 56.3; H, 6.4; N, 9.4.

PREPARATION 13

6- and 7-(mixture) Chloro-1,4-benzodioxan-2-carboxylic acid (A) Chlorine gas was passed into a stirred ice cold solution of methyl 1,4-benzodioxan-2-carboxylate (10 g.) in chloroform (100 ml.) in the presence of aluminum chloride (0.06 g.). The reaction was stopped after 20 minutes then the solution purged with nitrogen, washed with water, sodium bicarbonate solution, then water again, dried ($Na_2SO_4$) and evaporated in vacuo to leave a mixture (1:1 1 by $C^{13}$NMR spectroscopy) of methyl 6- and 7-chloro-1,4-benzodioxan-2-carboxylate (12.0 g.).

(B) A sample of the above product (1.4 g.) in ethanol (20 ml.) was treated with a solution of sodium hydroxide (0.25 g.) in water (1 ml.) at room temperature when a black coloration developed. After 48 hours at room temperature, the mixture was concentrated in vacuo, diluted with water, extracted with chloroform and the chloroform layer discarded. The aqueous phase was acidified with concentrated hydrochloric acid, extracted with chloroform, then the combined extracts dried ($MgSO_4$) and evaporated in vacuo to give a mixture (1.0 g.) of 6- and 7-chloro-1,4-benzodioxan-2-carboxylic acid, m.p. 145°–146° C., with consistent spectroscopic properties.

PREPARATION 14

2-Methyl-1,4-benzodioxan-2-carboxylic Acid

Jones' reagent (33.3 ml.) was added dropwise to a stirred solution of 2-hydroxymethyl-2-methyl-1,4-benzodioxan (5 g.) in acetone (300 ml.) at 5° C., then the reaction was allowed to attain room temperature. Isopropanol (10 ml.) was then added followed by water (200 ml.), the solution extracted with chloroform and the extracts evaporated in vacuo. The residual oil was taken up in chloroform (200 ml.) then extracted with dilute sodium bicarbonate solution and the aqueous phase further washed with chloroform. The aqueous phase was then acidified with hydrochloric acid, extracted with chloroform, the combined extracts washed with water, dried ($MgSO_4$) and evaporated in vacuo ti give 2-methyl-1,4-benzodioxan-2-carboxylic acid (1.7 g.). A sample was recrystallized from toluene, m.p. 133°–134° C.

Analysis %: Found: C, 61.8; H, 5.2. Calculated for $C_{10}H_{10}O_4$: C, 61.9; H, 5.2.

PREPARATION 15

6- and 7-(mixture)N,N-dimethylsulfamoyl-1,4-benzodioxan-2-carboxylic Acid (A) Catechol (180 g.) was added in portions to stirred sulfuric acid (138.5 ml.) so that the reaction temperature remained below 25° C. After addition was complete, the semi-solid mixture was heated at 45° C. for 60 minutes then cooled to room temperature and poured into ice-water (700 ml.). The solution was neutralized with solid barium carbonate, the barium sulfate collected, the filtrate acidified to pH 1 with concentrated sulfuric acid then refiltered. The filtrate was evaporated to leave crude 3,4-dihydroxybenzenesulfonic acid (182.40 g.) which was used without purification.

(B) The above product (182.40 g.) was acetylated in the standard manner using acetic anhydride (300 ml.) in pyridine (800 ml.) and the crude diacetoxy product (302.49 g.) used directly.

(C) Phosphorous pentachloride (378 g.) was added portionwise to a stirred solution of the pyridinium salt of 3,4-diacetoxy-benzene sulfonic acid (302.49 g.) in chloroform (1000 ml.) at 0° C. so that the reaction temperature did not rise above 15° C. After addition was complete, the reaction mixture was stirred at room temperature overnight then filtered, the chloroform solution evaporated in vacuo and the residual oil poured into ice water. The aqueous phase was extracted with chloroform, the combined extracts dried ($Na_2SO_4$) and evaporated in vacuo to leave a semi-solid residue which was recrystallized from carbon tetrachloride. This product (26.74 g.) was treated with aqueous dimethylamine (265 ml., 15% solution) at 20° C., the reaction left at room temperature overnight then the solution evaporated in vacuo. The dark residue was diluted with acetone (250 ml.), then decanted, the solution evaporated in vacuo and the residual oil stirred with an equal volume of sodium hydroxide solution at room temperature for 2 hours. The solution was then acidified with concentrated hydrochloric acid and the resulting product crystallized from water to give N,N-dimethyl-3,4-dihydroxybenzene sulfonamide, m.p. 142° C.

(D) A solution of sodium hydroxide (0.61 g.) in water (5 ml.) was added dropwise to a stirred suspension of the above product (3.0 gm.) and epichlorohydrin (1.43 ml.) in water (15 ml.) then the reaction was heated at 80° C. for 1½ hours. After cooling, the reaction was extracted with methylene chloride, the combined extracts washed with water, dried ($Na_2SO_4$) and evaporated to leave a mixture of 6- and 7-N,N-dimethylsulfamoyl-2-hydroxymethyl-1,4-benzodioxan (2.84 g.) as a sticky oil with consistent spectroscopic properties.

(E) Potassium permanganate (2.15 g.) was added in three portions to a stirred suspension of the above alcohol (2.8 g.) in potassium hydroxide solution (0.59 g. in 20 ml. water) and acetone (10 ml.) at 5° C. so that the reaction temperature did not rise above 10° C. The reaction was left at room temperature for 3 hours then the acetone evaporated and further potassium permanganate (1.5 g.) added followed by stirring overnight. Finally, more potassium permanganate (3.0 g.) was added and the reaction stirred at 35°–40° C. under nitrogen overnight. The resulting manganese dioxide was then collected, washed with water, the combined filtrates acidified with concentrated hydrochloric acid and extracted with chloroform. The combined extracts were washed with sodium hydroxide solution (5 N 2×40 ml.), the alkaline phase acidified with concentrated hydrochloric acid, extracted with chloroform and the combined extracts washed with water, dried ($Na_2SO_4$) and evaporated in vacuo. The crude product (0.46 g.) was combined with similar material (0.21 g.) obtained from re-extraction of the original manganese dioxide to give a mixture of 6- and 7-N,N-dimethylsulfamoyl-1,4-benzodioxan-2-carboxylic acid (0.67 g.), m.p. 156°–162° C.

Analysis %: Found: C, 45.5; H, 4.6; N, 4.90. Calculated for $C_{11}H_{13}NO_6S$: C, 46.0; H, 4.6; N, 4.9.

PREPARATION 16 cis and trans Ethyl 3-methyl-1,4-benzodioxan-2-carboxylate

These compounds were separated from each other by preparative HPLC and were identified by NMR spectroscopy according to published data (see e.g. *J. Med. Chem.*, 10, 880, 1967). Each isomer was hydrolyzed to the corresponding acid which was converted to the acid chloride without further characterization.

PREPARATION 17

4-Amino-6,7-dimethoxy-2-(3-methylpiperazin-1-yl)quinazoline

4-Amino-2-chloro-6,7-dimethoxyquinazoline (8.05 g.) and 2-methylpiperazine (10 g.) were heated under reflux in butanol for 15 hours. The reaction was then evaporated in vacuo and the residual oil was taken up in chloroform (200 ml.), washed with water (4×50 ml.), dried ($Na_2SO_4$) and evaporated in vacuo. The residual oil (13 g.) was recrystallized from isopropanol to give 4-amino-6,7-dimethoxy-2-(3-methylpiperazin-1-yl)quinazoline hemihydrate (3.0 g.), m.p. 185°–187° C.

Analysis %: Found: C, 58.1; H, 6.8; N, 22.8. Calculated for $C_{15}H_{21}N_5O_2 \cdot \frac{1}{2}H_2O$: C, 57.7; H, 7.1; N, 22.4.

PREPARATION 18

Mixture of 6- and 7-carbethoxy-1,4-benzodioxan-2-carboxylic Acid (A) Sodium hydroxide solution (1.94 g. in 16 ml. water) was added dropwise at room temperature to a stirred suspension of epichlorohydrin (4.6 ml.) and ethyl 3,4-dihydroxybenzoic acid (8 g.) when a solution resulted. The reaction was then heated at 80° C. for 1½ hours, cooled and extracted with dichloromethane, the extracts washed with water, dried ($Na_2SO_4$) and evaporated in vacuo to leave a mixture of 6- and 7-carbethoxy-2-hydroxymethyl-1,4-benzodioxan (10.87 g.) as a sticky oil with consistent spectroscopic properties.

(B) The above alcohol (5.0 g.) was oxidized with Jones reagent (12.3 ml.) in acetone (70 ml.) as described previously (Preparation 9) to give a mixture (2:1 by HPLC) of 6- and 7-carbethoxy-1,4-benzodioxan-2-carboxylic acid (1.78 g.) with consistent spectroscopic properties.

PREPARATION 19

Mixture of 6- and 7-carbamoyl-1,4-benzodioxan-2-carboxylic Acid (A) A stirred suspension of potassium carbonate (5.6 g.) and 4-cyanocatechol (2.7 g.) in acetone (50 ml.) was heated under reflux for ¼ hour then methyl 2,3-dibromopropionate (4.9 g.) was added dropwise. The resulting mixture was heated under reflux for 48 hours, then evaporated in vacuo, the residue diluted with water and extracted with chloroform. The combined extracts were washed with water, dried ($MgSO_4$) and evaporated in vacuo to give a mixture of methyl 6- and 7-cyano-1,4-benzodioxan-2-carboxylate (1.0 g.). A sample was recrystallized from isopropanol, m.p. 95°–96° C.

Analysis %: Found: C, 60.2; H, 4.2. Calculated for $C_{11}H_9NO_4$: C, 60.25; H, 4.2.

HPLC analysis of the crude product mixture showed a mixture of two components in the ratio of 5:2.

(B) Sodium hydroxide solution (0.7 ml., 6 N) and hydrogen peroxide (1 ml., 30%) were added dropwise to a stirred suspension of the above cyano-ester (0.5 g.) in ethanol (4 ml.) at 15° C. The mixture was then heated at 40°–50° C. for 2 hours, cooled, acidified with concentrated hydrochloric acid, the product collected and recrystallized from methanol/ethanol/water to give a mixture of 6- and 7-carbamoyl-1,4-benzodioxan-2-carboxylic acid, m.p. 258°–260° C.

Analysis %: Found: C, 53.2; H, 4.1; N, 6.4. Calculated for $C_{10}H_9NO_5$: C, 53.8; H, 4.1; N, 6.3.

What we claim is:

1. A compound of the formula

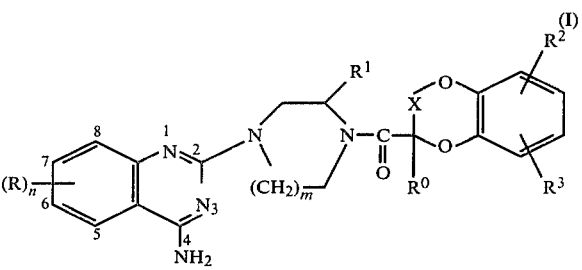

wherein
$(R)_n$ is selected from the group consisting of 6,7-di(lower alkoxy) or 6,7,8-tri(lower alkoxy);
m is 1 or 2;
X is selected from the group consisting of —$CHR^1$— or —$CH_2CH_2$—;
each of $R^1$ and $R^0$ is selected from the group consisting of hydrogen or lower alkyl;
and $R^2$ and $R^3$, which may the same or different, are selected from the group consisting of hydrogen, lower alkyl, lower alkoxy, halogen, lower alkanoyl, lower alkoxycarbonyl or a group of the formula —$CONR^4R^5$ or —$SO_2NR^4R^5$ wherein $R^4$ and $R^5$, which may the same or different, are selected from the group consisting of hydrogen or lower alkyl; and the pharmaceutically acceptable acid addition salts thereof.

2. A compound according to claim 1 wherein each of $R^0$ and $R^1$ is independently H or $CH_3$; and $R^2$ and $R^3$ are each independently hydrogen, lower alkyl, lower alkoxy, halogen, lower alkanoyl, lower alkoxycarbonyl, —$CONH_2$ or —$SO_2N(CH_3)_2$.

3. A compound according to claim 2 wherein $R^1$ is H or $CH_3$;
each of $R^2$ and $R^3$ is hydrogen, lower alkyl, lower alkoxy, halogen or lower alkanoyl; $(R)_n$ is 6,7-dimethoxy and the pharmaceutically acceptable acid addition salts thereof; said compound having the formula

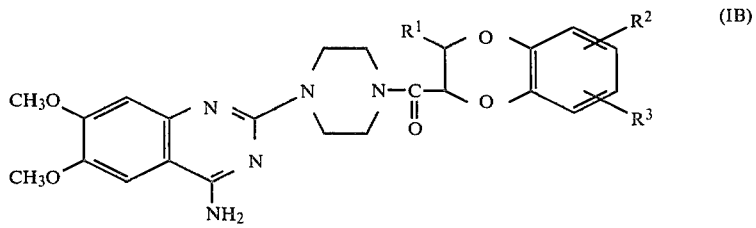

4. 4-Amino-2-[4-(1,4-benzodioxan-2-carbonyl)piperazin-1-yl]-6,7,8-trimethoxyquinazoline, the compound according to claim 2 wherein $R_n$ is 6,7,8-trimethoxy and each of $R^0$, $R^1$, $R^2$ and $R^3$ is hydrogen.

5. 4-Amino-2-[4-(1,4-benzodioxan-2-carbonyl)piperazin-1-yl]-6,7-dimethoxyquinazoline, the compound according to claim 3 wherein each of $R^1$, $R^2$ and $R^3$ is hydrogen.

6. A pharmaceutical composition comprising a cardiovascular regulating amount of a compound according to claim 1 or a pharmaceutically acceptable acid addition salt thereof together with a pharmaceutically acceptable diluent or carrier.

* * * * *

UNITED STATES PATENT AND TRADEMARK OFFICE

CERTIFICATE EXTENDING PATENT TERM
UNDER 35 U.S.C. 156

Patent No.     : 4,188,390

Dated          : February 12, 1980

Inventor(s)    : Simon F. Campbell

Patent Owner   : Pfizer, Inc.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 U.S.C. 156 (b).

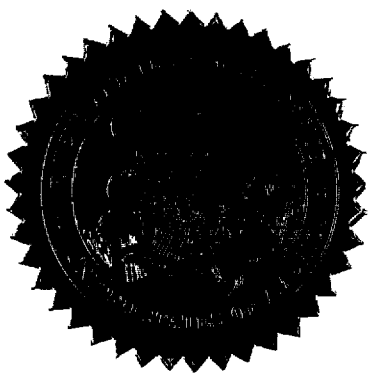

I have caused the seal of the Patent and Trademark Office to be affixed this 30th day of December 1991.

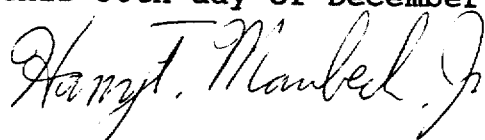

Harry F. Manbeck, Jr.
Assistant Secretary and Commissioner
  of Patents and Trademarks